United States Patent
Mitchell et al.

(10) Patent No.: US 6,503,992 B2
(45) Date of Patent: Jan. 7, 2003

(54) PHOSPHOROUS-CONTAINING MONOMERS AND FLAME RETARDANT HIGH IMPACT MONOVINYLIDENE AROMATIC POLYMER COMPOSITIONS DERIVED THEREFROM

(75) Inventors: Steven R. Mitchell, Akron, OH (US); H. James Harwood, Stow, OH (US); William G. Stobby, Mt. Pleasant, MI (US); Duane B. Priddy, Midland, MI (US); Kyung W. Suh, Midland, MI (US)

(73) Assignees: The Dow Chemical Company, Midland, MI (US); The University of Akron, Akron, OH (US)

( * ) Notice: Subject to any disclaimer, the term of this patent is extended or adjusted under 35 U.S.C. 154(b) by 0 days.

(21) Appl. No.: 09/912,083

(22) Filed: Jul. 24, 2001

(65) Prior Publication Data

US 2002/0040120 A1 Apr. 4, 2002

Related U.S. Application Data

(60) Provisional application No. 60/220,927, filed on Jul. 26, 2000.

(51) Int. Cl.[7] .............................................. C08F 130/02
(52) U.S. Cl. ..................... 526/278; 526/262; 526/272; 526/274; 526/275; 526/277; 526/318.4; 526/329.2; 526/342; 526/347
(58) Field of Search .................................. 526/262, 275, 526/274, 277, 272, 278, 318.4, 329.2, 342, 347

(56) References Cited

U.S. PATENT DOCUMENTS

| | | | |
|---|---|---|---|
| 3,123,655 A | 3/1964 | Otting et al. | |
| 3,346,520 A | 10/1967 | Lee | |
| 3,639,522 A | 2/1972 | Narayana et al. | |
| 4,409,369 A | 10/1983 | Lyons et al. | |
| 4,572,819 A | 2/1986 | Priddy et al. | |
| 4,585,825 A | 4/1986 | Wesselmann | |
| 4,666,987 A | 5/1987 | Burmester et al. | |
| 5,240,993 A | 8/1993 | Aerts et al. | |

FOREIGN PATENT DOCUMENTS

EP  0096447  6/1983

*Primary Examiner*—Helen L. Pezzuto

(57) ABSTRACT

Disclosed are cyclic phosphate esters of fumarate- or maleic acids suitable for use as a comonomer, capable of being copolymerized with a monovinylidene aromatic compounds to impart flame resistant properties to the resultant copolymers.

11 Claims, No Drawings

PHOSPHOROUS-CONTAINING MONOMERS AND FLAME RETARDANT HIGH IMPACT MONOVINYLIDENE AROMATIC POLYMER COMPOSITIONS DERIVED THEREFROM

CROSS REFERENCE STATEMENT

This application claims the benefit of U.S. Provisional Application No. 60/220,927, filed Jul. 26, 2000.

BACKGROUND OF THE INVENTION

The present invention relates to a number of novel phosphorus-containing monomers capable of imparting flame resistant properties to certain high impact polymer compositions synthesized using such monomers.

Polymers derived from a monovinylidene aromatic compound, such as styrene, have successfully been used commercially in numerous end-use applications for a number of years. Such polymers include the high impact modifications thereof in which the impact strength is improved by incorporating a minor amount of a toughening agent, such as a suitable rubber, during the polymerization. One major disadvantage of such polymers is their inherent high flammability. A well-known approach to deal with the flammability has been to incorporate various flame retardant additives to the polymers. A well-known group of such additives are certain halogenated flame retardant organic compounds such as decabromodiphenyloxide.

When such halogenated organic compounds are blended with polymers derived from a monovinylidene aromatic compound, the flammability of the resultant polymer compositions is significantly diminished. However, such halogenated compounds also present potential problems associated with toxicity and environmental impact. To overcome such problems, certain phosphorus-containing compounds such as triphenylphosphate have been used in lieu of halogenated compounds. Despite their proven utility as flame retardant additives for polymers of a monovinylidene aromatic compound, such phosphorus-containing compounds have several known disadvantages. More particularly, such compounds have a tendency to be volatilized and thereby lose their overall effectiveness as flame retardant additives, when polymers blended therewith are being fabricated into useful articles. Such compounds also tend to migrate to the surface of fabricated articles and plate out on the surface of polymer processing equipment in a phenomenon known in the trade as "juicing." Further, any extra amounts of such compounds used in polymer blends to compensate for the loss of their effectiveness because of the known volatility often tend to plasticize polymer blends thereby adversely impacting certain physical properties thereof such as heat resistance.

Therefore, it remains highly desirable to obtain a monovinylidene aromatic polymer composition having effective flame resistance without disadvantages of previous attempts therefor and related flame retardant additives known in the prior art.

SUMMARY OF THE INVENTION

One aspect of the present invention is a phosphorus-containing compound suitable for use as a comonomer, capable of being copolymerized with monovinylidene aromatic compounds to impart flame resistant properties to the resultant copolymers thereof, comprising compounds of a generic formula:

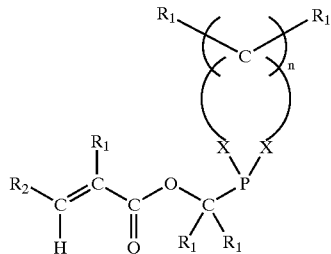

$R_1$ is hydrogen or an alkyl;
$R_2$ is carboalkoxy;
X is oxygen, sulfur or alkylamine;
P is trivalent phosphorus; and
n is 2 or 3.

Another aspect of the present invention is the phosphorus-containing compound of the generic formula above wherein R2 is a radical having a generic formula:

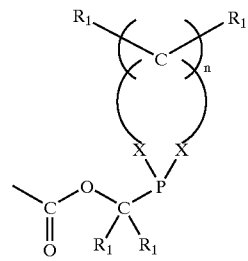

wherein:
$R_1$ is hydrogen or an alkyl;
X is oxygen, sulfur or alkylamine;
P is trivalent phosphorus; and
n is 2 or 3.

Yet another aspect of the present invention is a phosphorus-containing compound suitable for use as a comonomer, capable of being copolymerized with a monovinylidene aromatic compounds to impart flame resistant properties to the resultant copolymers thereof, comprising compounds of a generic formula:

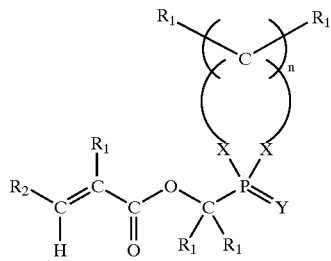

wherein:
$R_1$ is hydrogen or an alkyl;
$R_2$ is carboalkoxy;
X is oxygen, sulfur or alkylamine;

Y is oxygen or sulfur;

P is pentavalent phosphorus; and n is 2 or 3.

Another aspect of the present invention is the phosphorus-containing compound of the generic formula above wherein R2 is a radical having a generic formula:

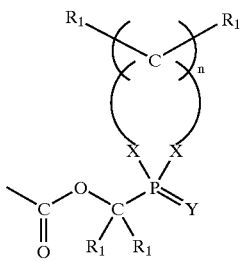

wherein:

$R_1$ is hydrogen or an alkyl;

X is oxygen, sulfur or alkylamine;

Y is oxygen or sulfur;

P is pentavalent phosphorus; and n is 2 or 3.

Another aspect of the present invention is a flame retardant (co) polymer composition of a monovinylidene aromatic compound a phosphorus-containing compound of the generic formula, which may be toughened or modified with rubber or other elastomers.

DETAILED DESCRIPTION OF INVENTION

Phosphorus-containing monomers of the present invention can generally be categorized as cyclic phosphonite or phosphonate containing esters of fumaric and maleic acid. Synthesis of relevant monomers or compounds of the present invention are well within the capabilities of those skilled in the art.

Examples of useful compounds of the present invention, as identified in accordance with the nomenclature system of Chemical Abstracts, include, without limitation: 2-Butenedioic acid (2E)-, bis[(5,5-dimethyl-1,3,2-dioxaphosphorinan-2-yl)methyl]ester; 2-Butenedioic acid: 2-methyl-, 4-[(5,5-dimethyl-1,3,2-dioxaphosphorinan -2-yl) methyl]1-methyl ester, (2E)-; 2-Propenoic acid, (5,5-dimethyl-2-oxido-1,3,2-dioxaphosphorinan-2-yl)methyl ester; 2-Propenoic acid, 2-methyl -,(4,4,5,5-tetramethyl-1,3, 2-dioxaphospholan-2-yl)methyl ester; 2-Propenoic acid, 1-(5,5-dimethyl-2-sulfido-1,3,2-dioxaphosphorinan-2-yl) ethyl ester; and 2-Propenoic acid, (tetrahydro-1,3,5,5-tetramethyl-2-oxido-1,3,2-diazaphosphorin-2(1H)-yl) methyl ester.

Monovinylidene aromatic polymers suitable for use as a matrix in the preparation of the rubber modified monovinylidene aromatic polymer are those produced by polymerizing a vinyl aromatic monomer. Vinyl aromatic monomers include, but are not limited to those described in U.S. Pat. Nos. 4,666,987, 4,572,819 and 4,585,825, which are herein incorporated by reference. Preferably, the monomer is of the formula:

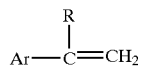

wherein R is hydrogen or methyl, Ar is an aromatic ring structure having from 1 to 3 aromatic rings with or without alkyl, halo, or haloalkyl substitution, wherein any alkyl group contains 1 to 6 carbon atoms and haloalkyl refers to a halo substituted alkyl group. Preferably, Ar is phenyl or alkylphenyl, wherein alkylphenyl refers to an alkyl substituted phenyl group, with phenyl being most preferred. Typical vinyl aromatic monomers which can be used include: styrene, alpha-methylstyrene, all isomers of vinyl toluene, especially paravinyltoluene, all isomers of ethylstyrene, propylstyrene, vinyl biphenyl, vinyl naphthalene, vinyl anthracene and the like, and mixtures thereof. The vinyl aromatic monomers may also be combined with other copolymerizable monomers. Examples of such monomers include, but are not limited to acrylic monomers such as acrylonitrile, methacrylonitrile, methacrylic acid, methyl methacrylate, acrylic acid, and methyl acrylate; maleimide, n-phenylmaleimide, and maleic anhydride. These copolymerizable monomers can be used alone or in combination. For example, a phosphorus-containing compound of the present invention can be copolymerized with a monovinylidene aromatic compound in combination with at least one copolymerizable monomer(s) to produce copolymers of the present invention. A preferred copolymerizable monomer is acrylonitrile. A preferred combination of copolymerizable monomers comprise acrylonitrile and n-phenylmaleimide.

The polymerization of the vinyl aromatic monomer is conducted in the presence of predissolved elastomer to prepare impact modified, or grafted rubber containing products. Rubber modified vinyl aromatic polymers can be prepared by polymerizing the vinyl aromatic monomer in the presence of a predissolved rubber to prepare impact modified, or grafted rubber containing products, examples of which are described in U.S. Pat. Nos. 3,123,655, 3,346,520, 3,639,522, and 4,409,369 which are herein incorporated by reference. The rubber is typically a butadiene or isoprene rubber, preferably polybutadiene. Preferably, the rubber modified vinyl aromatic polymer is high impact polystyrene (HIPS) or acrylonitrile-butadiene-styrene (ABS), with HIPS being most preferred.

The rubber particles typically have a volume average particle size of from 0.2 to 3.0 microns. If a bimodal particle size is produced, the rubber typically comprises from approximately 80 to 85 weight percent of the aforementioned particles and from about 5 to 20 weight percent of particles having a volume average particle size of from 2 to 6 microns.

The polymerization is preferably conducted in the presence of an initiator. Suitable initiators include any initiator capable of imparting the desired grafting of polymer to the rubber particle under the conditions of polymerization and accelerating the polymerization of the vinyl aromatic monomer. Representative initiators include peroxide initiators such as peresters, e.g. tertiary butyl peroxybenzoate and tertiary butyl peroxyacetate, tertiary butyl peroxyoctoate, dibenzoyl peroxide, dilauroyl peroxide, 1,1-bis tertiarybutyl peroxycyclohexane, 1-3-bis tertiarybutylperoxy-3,3,5-trimethyl cyclohexane, di-cumyl peroxide, and the like.

Photochemical initiation techniques can be employed if desired. Preferred initiators include tertiary butyl peroctoate, tertiary butyl isopropyl percarbonate, dibenzoyl peroxide, tertiary butyl peroxy benzoate, 1,1-bistertiarybutylperoxy cyclohexane and tertiarybutylperoxy acetate.

Initiators may be employed in a range of concentrations dependent on a variety of factors including the specific initiators employed, the desired levels of polymer grafting and the conditions at which the mass polymerization is conducted. Typically, initiators may be employed in amounts from 0 to 2000, preferably from 100 to 1500, parts by weight per million parts by weight of vinyl aromatic monomer.

Additionally, a solvent may be used in the polymerization. Acceptable solvents include normally liquid organic materials which form a solution with the rubber, vinyl aromatic monomer and the polymer prepared therefrom. Representative solvents include substituted aromatic hydrocarbons such as ethylbenzene, toluene, xylene or the like; substituted or unsubstituted, straight or branched chain saturated aliphatics of 5 or more carbon atoms, such as heptane, hexane, octane or the like; alicyclic or substituted alicyclic hydrocarbons having 5 or 6 carbon atoms, such as cyclohexane; and the like. Preferred solvents include substituted aromatics, with ethylbenzene and xylene being most preferred. In general, the solvent is employed in amounts sufficient to improve the processability and heat transfer during polymerization. Such amounts will vary depending on the rubber, monomer and solvent employed, the process equipment and the desired degree of polymerization. If employed, the solvent is generally employed in an amount of up to about 35 weight percent, preferably from about 2 to about 25 weight percent, based on the total weight of the solution.

Other materials may also be present in the process of preparing the rubber modified monovinylidene aromatic polymer composition, including plasticizers, e.g. mineral oil; flow promoters, lubricants, antioxidants, catalysts, mold release agents, or polymerization aids such as chain transfer agents, including alkyl mercaptans, e.g. n-dodecyl mercaptan. If employed, a chain transfer agent can be present in an amount of from about 0.001 to about 0.5 weight percent based on the total weight of the polymerization mixture to which it is added.

The temperature at which the polymerization is conducted will vary according to the specific components, particularly initiator, but will generally vary from about 60 to about 190° C.

Crosslinking of the rubber in the resulting product and removal of the unreacted monomers, as well as any solvent, if employed, and other volatile materials is advantageously conducted employing conventional techniques, such as introducing the polymerization mixture into a devolatilizer, flashing off the monomer and other volatiles at elevated temperature, e.g. from 200 to 300° C. under vacuum and removing them from the devolatilizer.

Typically, a bimodal composition is produced by polymerizing a feed of the desired components and a grafting initiator in a series of reactors, wherein the rubber particles are formed and stabilized within the first reactor, then fed to the top of a second reactor, wherein a second feed is added. The second feed may already contain sized rubber particles or may be another monomer/rubber raw material feed which will produce large particles. Methods of preparing bimodal particle size polymers are disclosed in U.S. Pat. No. 5,240,993, which is incorporated herein by reference, and in EP-0096447.

As used herein, the volume average particle size refers to the diameter of the rubber particles, including all occlusions of vinyl aromatic polymer within the rubber particles. Volume average particle sizes and distributions may be measured using conventional techniques such as a Coulter Counter™, transmission electron microscopy.

The phosphorus-containing compound in the flame retardant copolymer of the present invention is employed in amounts of at least about one (1) parts by weight, preferably at least about two (2) parts by weight, and more preferably at least about five (5) parts by weight based on 100 parts by weight of the polymer composition of the present invention. In general, the phosphorus-containing compound in the flame retardant copolymer of the present invention is amounts less than or equal to about thirty (30) parts by weight, preferably less than or equal to about fifteen (15) parts by weight, more preferably less than or equal to about 13 parts by weight, and most preferably less than or equal to about ten (10) parts by weight based on 100 parts by weight of the copolymer of the present invention.

In addition, the flame retardant polymer compositions may also optionally contain one or more additives that are commonly used in polymers of this type. Preferred additives of this type include, but are not limited to: antioxidants; impact modifiers; plasticizers, such as mineral oil; antistats; flow enhancers; mold releases; fillers, such as calcium carbonate, talc, clay, mica, wollastonite, hollow glass beads, titanium oxide, silica, carbon black, glass fiber, potassium titanate, single layers of a cation exchanging layered silicate material or mixtures thereof, and perfluoroalkane oligomers and polymers (such as polytetrafluoroethylene) for improved drip performance in UL 94. Further, compounds which stabilize flame retardant polymer compositions against degradation caused by, but not limited to heat, light, and oxygen, or a mixture thereof may be used.

If used, the amount of such additives will vary and need to be controlled depending upon the particular need of a given end-use application, which can easily and appropriately be exercised by those skilled in the art.

The flame retardant copolymers of this invention are thermoplastic. When softened or melted by the application of heat, the flame retardant polymer compositions of this invention can be formed or molded using conventional techniques such as compression molding, injection molding, gas assisted injection molding, calendering, vacuum forming, thermoforming, extrusion and/or blow molding, alone or in combination. The flame retardant polymer compositions can also be formed, spun, or drawn into films, fibers, multi-layer laminates or extruded sheets, or can be compounded with one or more organic or inorganic substances, on any machine suitable for such purpose.

The copolymers of the present invention are useful to fabricate numerous useful articles and parts. Some of the articles which are particularly well suited include television cabinets, computer monitors, related printer housings which typically are required to have excellent flammability ratings.

The following examples are provided to further illustrate the invention and should not be construed as limiting its scope.

EXAMPLES

Example 1
Bis(2-oxo-5,5-dimethyl-1,3,2-dioxaphosphorinanylmethyl) Fumarate (ODDPM Fumarate)

ODDPM alcohol (36.03 g, 02.00 mole) was added to 100 mL of dry chloroform in a 3-neck, 250 mL round bottom flask. The middle neck was fitted with a reflux condenser which was fitted with a drying tube containing sodium sulfate. The outer necks were fitted with glass stoppers. The mixture was stirred with a magnetic stirbar, and when the ODDPM alcohol had fully dissolved in the chloroform, fumaryl chloride (15.30 g, 0.100 mole) was added all at once to the solution. The mixture was detected by sampling the atmosphere above the condenser with pHydrion paper (pH 0–13). The pH paper turned deep red which indicated a pH of 0. Also, after five hours of reaction time, an increase in solution viscosity was observed relative to that of the initial solution. The solution was then allowed to cool to room temperature, and 75 mL of chloroform was added to the flask. The solution was transferred to a 250 mL separatory funnel and added dropwise to a large excess of benzene. A white translucent solid precipitated from the benzene which was collected by Büchner filtration, washed with benzene, and dried in a vacuum oven overnight at 60° C. The yield of ODDPM methacrylate was 39.0 g (89 percent). The ODDPM methacrylate (m.p. 149.5–150° C.) was purified by recrystallization from benzene/chloroform.

Example 2
Copolymerization of Styrene and Bis(2-Oxo-5,5-dimethyl-1,3,2-dioxaphosphorinanylmethyl)Fumarate ODDPM fumarate is not soluble in non-polar hydrocarbon solvents, but has sufficient solubility in halogenated solvents such as chloroform. The copolymerization solutions were prepared in round bottom flasks by first adding the appropriate amount of AIBN from an AIBN standard solution made from 0.200 g AIBN and 29.8 g chloroform. Then, the monomers were added followed by dilution with chloroform (Table 1). For the copolymerizations with comonomer feed compositions of greater than 10 mole percent ODDPM fumarate homogeneous solution could only be achieved at elevated temperatures. The round bottom flasks were capped with rubber septa, which were fastened tightly to the flasks with copper wire. Prior to polymerization, each solution was sparged with $N_2$ for 10 minutes while being chilled with ice water. The flasks were then placed in an oil bath at 60° C. (+/−0.5° C.) for the times given in Table 1. The copolymerization solutions were concentrated on a Rotovapor apparatus and added to a large excess of methanol to precipitate the copolymers. The copolymers were collected by gravity filtration, washed with methanol, and dried in a vacuum oven at approximately 80° C. overnight. The poly(styrene-co-ODDPM fumarate) samples were dissolved in chloroform and purified further by reprecipitation in diethyl ether. Finally, the copolymers were collected by gravity filtration, washed with diethyl ether, and dried in a vacuum oven at approximately 80° C. overnight. The copolymers all had a powdery texture.

TABLE 1

Formulations for the Copolymerizations[1] of Styrene and ODDPM Fumarate at 60° C.

| Mole % ODDPM Fumarate in Feed | Styrene (g)/(mol) | ODDPM Fumarate (g)/(mold) | $CHCl_3$ (g) | Reaction Time (hr.) |
|---|---|---|---|---|
| 5 | 2.47/2.38 × $10^{-2}$ | 0.55/1.25 × $10^{-3}$ | 25.7 | 7.5 |
| 10 | 2.34/2.25 × $10^{-2}$ | 1.10/2.50 × $10^{-3}$ | 25.3 | 9.0 |
| 15 | 2.21/2.13 × $10^{-2}$ | 1.65/3.75 × $10^{-3}$ | 24.9 | 7.5 |
| 20 | 2.08/2.00 × $10^{-2}$ | 2.20/5.00 × $10^{-3}$ | 24.5 | 7.0 |
| 30 | 1.82/1.75 × $10^{-2}$ | 3.30/7.50 × $10^{-3}$ | 23.6 | 6.5 |

[1]Each system contained 0.008 g (0.20 mole percent) AIBN

What is claimed is:

1. A copolymer comprising a monovinylidene aromatic compound and a phosphorus containing compound selected from a) a phosphorus-containing compound suitable for use as a comonomer, capable of being copolymerized with a monovinylidene aromatic compound to impart flame resistant properties to the resultant copolymers thereof, comprising compounds of a generic formula:

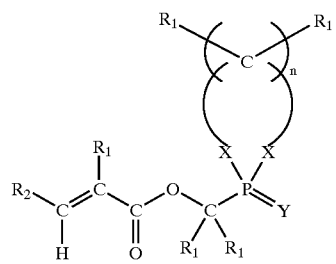

wherein:

$R_2$ is carboalkoxy or a radical of generic formula:

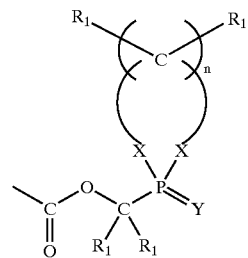

$R_1$ is hydrogen or an alkyl;

X is oxygen, sulfur or alkylamine;

Y is oxygen or sulfur;

P is pentavalent phosphorus; and n is 2 or 3; and b) a phosphorus-containing compound suitable for use as a comonomer, capable of being copolymerized with a monovinylidene aromatic compound to impart flame resistant properties to the resultant copolymers thereof, comprising compounds of a generic formula:

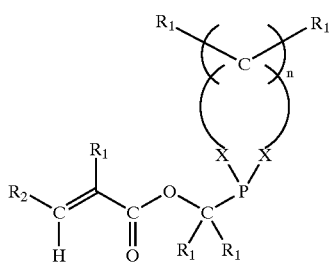

wherein:
$R_2$ is carboalkoxy or a radical of generic formula:

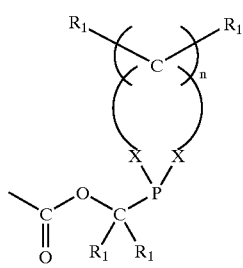

$R_1$ is hydrogen or an alkyl;
X is oxygen, sulfur or alkylamine;
P is trivalent phosphorus; and
n is 2 or 3.

2. A copolymer of claim 1 wherein the monovinylidene aromatic compound is styrene.

3. A copolymer of claim 1 which is modified with rubber.

4. A copolymer of claim 3 wherein the rubber is polybutadiene.

5. A copolymer of claim 2 which is modified with rubber.

6. A copolymer of claim 5 wherein the rubber is polybutadiene.

7. The copolymer of claim 1 additionally comprising at least one copolymerizable compound selected from the group consisting of acrylonitrile, methacrylonitrile, methacrylic acid, methyl methacrylate, acrylic acid, and methyl acrylate; maleimide, n-phenylmaleimide, and maleic anhydride.

8. The copolymer of claim 1 additionally comprising acrylonitrile and n-phenylmaleimide.

9. An article produced from the rubber modified copolymer of claim 3.

10. An article produced from the copolymer of claim 7.

11. An article produced from the copolymer of claim 8.

* * * * *